(12) United States Patent
Koike

(10) Patent No.: US 8,061,218 B2
(45) Date of Patent: *Nov. 22, 2011

(54) FLUID FLOW DETECTOR

(75) Inventor: Kazuhiro Koike, Shizuoka-ken (JP)

(73) Assignee: Tyco Healthcare Group LP, Mansfield, MA (US)

( * ) Notice: Subject to any disclaimer, the term of this patent is extended or adjusted under 35 U.S.C. 154(b) by 170 days.

This patent is subject to a terminal disclaimer.

(21) Appl. No.: 12/542,020

(22) Filed: Aug. 17, 2009

(65) Prior Publication Data

US 2010/0071478 A1    Mar. 25, 2010

(30) Foreign Application Priority Data

Sep. 25, 2008 (JP) ................................ 2008-245141

(51) Int. Cl.
*G01F 1/22* (2006.01)
*A61M 5/00* (2006.01)
(52) U.S. Cl. ................... 73/861.57; 604/246; 73/861.52
(58) Field of Classification Search .................. None
See application file for complete search history.

(56) References Cited

U.S. PATENT DOCUMENTS

| | | | |
|---|---|---|---|
| 3,416,371 A * | 12/1968 | Locke | 73/861.57 |
| 4,486,744 A | 12/1984 | Pratt et al. | |
| 4,699,617 A * | 10/1987 | Moriuchi et al. | 604/246 |
| 5,019,678 A * | 5/1991 | Templeton et al. | 200/81.9 M |
| 5,445,622 A | 8/1995 | Brown | |
| 5,462,525 A | 10/1995 | Srisathapat et al. | |
| 5,820,715 A * | 10/1998 | Singleterry et al. | 156/73.1 |
| 6,915,706 B2 | 7/2005 | Rousselin | |
| 6,935,190 B1 | 8/2005 | Height et al. | |

OTHER PUBLICATIONS

Extended European search report of Jan. 7, 2010.

* cited by examiner

*Primary Examiner* — Harshad Patel
(74) *Attorney, Agent, or Firm* — Lisa E. Winsor, Esq.

(57) ABSTRACT

An upstream hole is formed at the upstream end of a detector main body of a liquid flow detector for detecting liquid flow, and a downstream hole is formed at the downstream end, with a liquid flow channel comprising a liquid flow detection channel, discharge channel, and, optionally, intermediate flow channel, being formed between the upstream hole and downstream hole. A mobile body which is optionally, spherical, moves with the flow of liquid, and is arranged inside the liquid flow channel. The diameter of the liquid flow detection channel is smaller than the diameter of the discharge channel, and the diameter of the mobile body is slightly smaller than the diameter of the liquid flow detection channel. The shape of the peripheral edge part of the upstream hole and the downstream hole is optionally elliptical.

14 Claims, 3 Drawing Sheets

FLUID FLOW DETECTOR

TECHNICAL FIELD OF THE DISCLOSURE

The present disclosure relates to a liquid flow detector for detecting the flow of a liquid in a transfusion line, and a transfusion line provided with same.

BACKGROUND OF THE DISCLOSURE

Liquids such as drug solutions are conventionally supplied to patients using a transfusion line provided with a tube. In such cases, it is difficult to visually confirm the flow of the liquid if there is a small amount of liquid to be administered to the patient. Furthermore, even if a liquid flow detector for detecting the flow of liquid is incorporated into the transfusion line, this liquid flow detector must be such that it does not obstruct administration of the liquid to the patient. In addition, there may be cases where the liquid flow detector is used only once, and an inexpensive liquid flow detector which does not utilize a device such as an electrical sensor or an optical sensor is required in such cases. There are instruments such as this in which a spherical body which moves along with the flow of liquid is provided in the liquid flow detector.

This liquid flow detector (flowmeter) has a configuration in which an inlet port extending horizontally and a conical upper flow channel extending vertically are connected by a narrow passage, and a spherical body is arranged inside the upper flow channel. The upper flow channel is formed so that the upper part has a somewhat larger diameter than the lower part, and the flow of the liquid can be detected by the position of the spherical body which moves inside the upper flow channel depending on the flow of liquid, which also allows the flow rate of the liquid to be measured.

However, with the conventional liquid flow detector described above, it is difficult to detect the flow of liquid if the liquid to be administered to the patient is in an extremely small amount, for example if the flow velocity is of the order of 1 ml per hour.

The present invention has been devised in view of the situation outlined above, and it aims to provide an inexpensive liquid flow detector which can detect the flow of a minute amount of liquid, and a transfusion line provided with same.

SUMMARY OF THE DISCLOSURE

The liquid flow detector according to the present disclosure is suitable for incorporation into a transfusion line to detect the flow of a liquid in the transfusion line. The liquid flow detector comprises: a detector main body in which is formed a liquid flow channel having a circular cross section and comprising, between an upstream hole formed at an upstream end and a downstream hole formed at a downstream end, a liquid flow detection channel positioned on the upstream hole side and a discharge channel positioned on the downstream hole side; and a mobile body which is placed inside the liquid flow channel, moving along with the flow of a liquid inside the liquid flow channel, and in which the outer peripheral edge part of the face orthogonal to the direction of movement is formed to be circular; the diameter of the liquid flow detection channel is set to be smaller than the diameter of the discharge channel, and the maximum diameter of the outer peripheral edge part of the face orthogonal to the direction of movement of the mobile body is set to be slightly smaller than the diameter of the liquid flow detection channel, and furthermore the upstream hole and the downstream hole are formed with a size and shape such that liquid flows through them without being obstructed by the mobile body, but the mobile body does not pass through them. Also disclosed is a transfusion line which includes the liquid flow detector of the disclosure.

Figure 1:
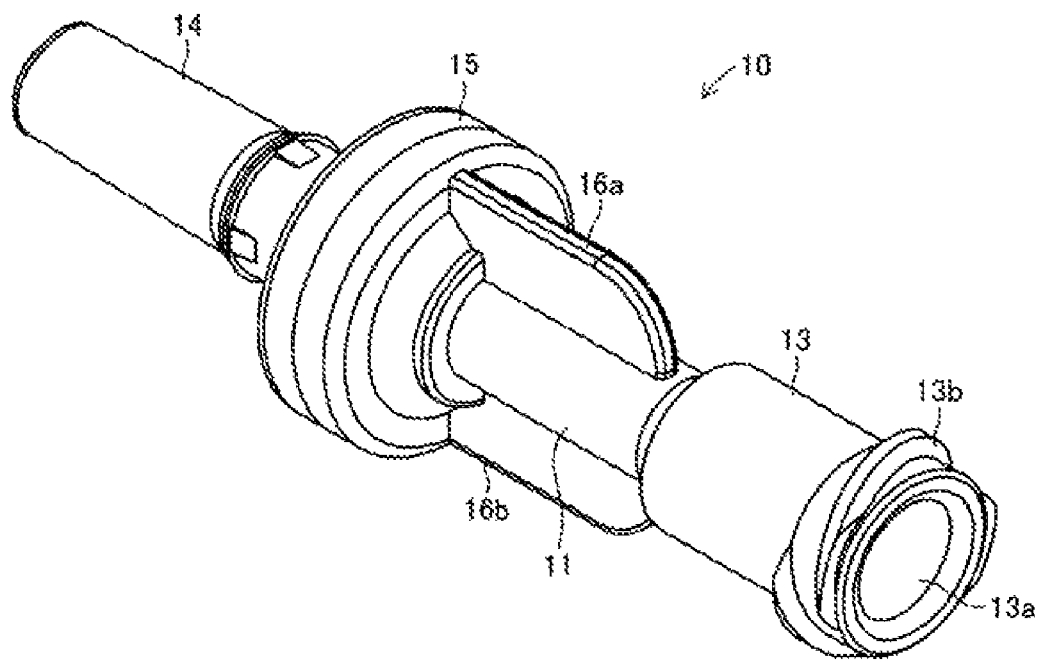
FIG. 1 is an oblique view showing the liquid flow detector according to the mode of embodiment of the present invention.

Corresponding reference numerals indicate corresponding parts throughout the drawings, and herein the following reference numerals apply:
10 . . . liquid flow detector; 11 . . . detector main body; 12 . . . mobile spherical body; 13 . . . inflow pipe; 14 . . . outflow pipe; 17 . . . liquid flow channel; 17a . . . liquid flow detection channel; 17b . . . discharge channel; 17c . . . intermediate flow channel; 18 . . . upstream hole; 19 . . . downstream hole; 20 . . . transfusion line set.

DETAILED DESCRIPTION OF THE DISCLOSURE

With the liquid flow detector according to the present disclosure configured in the manner described above, an upstream hole is provided at an upstream portion of the flow of liquid in the detector main body, and also a downstream hole is provided at a downstream portion, with a liquid flow channel comprising a liquid flow detection channel and a discharge channel being formed between said upstream hole and downstream hole. Furthermore, a mobile body is arranged inside the liquid flow channel in a state in which it cannot pass through the upstream hole and the downstream hole. As the mobile body in this case, it is possible to use a spherical body, a columnar body, a body in which the centre axis of two conical bodies has been placed coaxially and the tops of the two conical bodies are linked, or a body in which the centres of two facing discs are linked by a shaft, or similar. The diameter of the liquid flow detection channel is slightly greater than the diameter of the outer peripheral edge part of the mobile body, and the diameter of the discharge channel is even greater than the diameter of the liquid flow detection channel.

Accordingly, when the mobile body is positioned at an upstream portion of the liquid flow detection channel in a state in which the detector main body is arranged so that the liquid flow channel is horizontal, if the liquid flows inside the liquid flow channel from the upstream side towards the downstream side, the mobile body moves from the upstream side of the liquid flow detection channel towards the downstream side in accordance with the flow of liquid. This allows the flow of liquid inside the liquid flow channel to be detected. In this case, the smaller the area of the minimum gap between the inner peripheral surface of the liquid flow detection channel and the outer peripheral surface of the mobile body, the greater the detection accuracy possible (detection of an even smaller amount of flow). Then, if the mobile body moves from the liquid flow detection channel into the discharge channel, the gap between the inner peripheral surface of the discharge channel and the outer peripheral surface of the mobile body increases, and therefore the mobile body moves less (more slowly), or the mobile body reaches a static state. In this case, the mobile body does not obstruct the flow of liquid.

Moreover, even if the difference between the diameter of the liquid flow detection channel and the diameter of the outer peripheral edge part of the mobile body is made to be small and a minute amount of liquid flows inside the liquid flow detection channel, the mobile body presents resistance to the flow of liquid and is moved. This means that it is possible to obtain an inexpensive liquid flow detector which can detect an extremely small flow of liquid. That is to say, the expression "the diameter of the mobile body [is] set to be slightly smaller than the diameter of the liquid flow detection channel" according to the present disclosure means that the diameter of the outer peripheral edge part of the mobile body and the diameter of the liquid flow detection channel are set so that no more than the minimum area of gap needed for the mobile body to move horizontally in accordance with the flow of liquid can be ensured. The flow rate of liquid to be detected in this case should preferably be a smaller amount than the volume of liquid used for a normal drip (30 ml/h-120 ml/h). (0.1 ml/h-20 ml/h) is set as the reference, for example.

Furthermore, the upstream hole and the downstream hole are formed with a size and shape such that liquid flows through the upstream and downstream holes without being obstructed by the mobile body, but the mobile body does not pass through the upstream and downstream holes, and therefore it is possible to prevent the flow of liquid from stopping due to the mobile body abutting the whole peripheral edge part of the upstream hole or downstream hole. Moreover, the diameter of the liquid flow detection channel is preferably all the same from the upstream end as far as the downstream end, but the discharge channel may be such that the diameter at the downstream side is slightly greater than the diameter at the upstream side.

Further structural features of the liquid flow detector according to the present invention lie in the fact that the mobile body may consist of a spherical body. This means that the mobile body has a simple shape, and it is possible to detect liquid flow with good accuracy. Furthermore, the mobile body is preferably formed as a sphere which does not distort and the like, and it preferably consists of a material with a somewhat higher specific gravity than the liquid. This means that the movement of the mobile body is sensitive to the flow of liquid, enabling effective detection of the flow of liquid.

Further structural features of the liquid flow detector according to the present invention lie in the fact that an intermediate flow channel whereof the diameter becomes steadily greater from the liquid flow detection channel towards the discharge channel may be provided between the liquid flow detection channel and the discharge channel. This means that there is no difference in level between the liquid flow detection channel and the discharge channel which obstructs the movement of the mobile body. Consequently, when the liquid flow is being checked, if the specific gravity of the mobile body is higher than the specific gravity of the liquid, it is possible to smoothly carry out an operation to move the mobile body from the discharge channel to the liquid flow detection channel by inclining the liquid flow detector so that the discharge channel is positioned higher up than the liquid flow detection channel, and furthermore, if the specific gravity of the mobile body is lower than the specific gravity of the liquid, it is possible to smoothly carry out an operation to move the mobile body from the discharge channel to the liquid flow detection channel by inclining the liquid flow detector so that the discharge channel is positioned lower down than the liquid flow detection channel. This intermediate flow channel is especially effective when the diameter of the discharge channel is the same from upstream to downstream.

Further structural features of the liquid flow detector according to the present invention lie in the fact that the shape, from between the size and shape of the upstream hole and downstream hole such that liquid flows through the upstream and downstream holes without being obstructed by the mobile body, but the mobile body does not pass through the upstream and downstream holes, consists of a shape in which the peripheral edge part of the upstream hole and downstream hole orthogonal to the flow of liquid may be elliptical. This means that it is possible to reliably prevent the flow of liquid from stopping due to the mobile body coming into abutment with the peripheral edge part of the upstream hole and downstream hole.

Further structural features of the liquid flow detector according to the present invention include the possibility that an inflow pipe comprising a female luer which links in communication with the liquid flow channel is joined to the upstream hole side of the detector main body, and an outflow pipe comprising a male luer which links in communication with the liquid flow channel is joined to the downstream hole side of the detector main body. This means that the liquid flow detector can be incorporated into a transfusion line between an inflow pipe and an outflow pipe.

Furthermore, the structural features of the transfusion line according to the present invention lie in the fact that it is a transfusion line provided with a liquid flow detector, and it is provided with a liquid supply part and a liquid supply channel through which passes a liquid supplied from the liquid supply part, and the liquid flow detector is arranged in the liquid supply channel. This means that it is possible to obtain a transfusion line provided with an inexpensive liquid flow detector which can detect the flow of liquid.

DETAILED DESCRIPTION OF THE DRAWINGS

Figure 2:
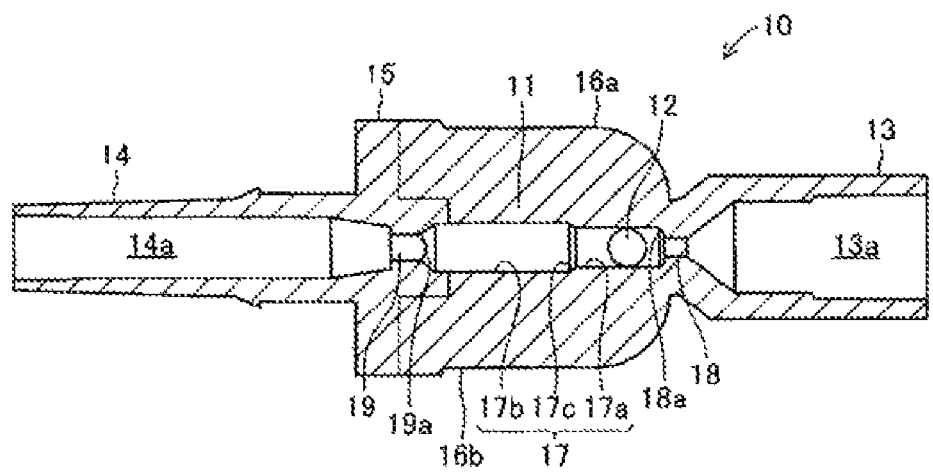
FIG. 2 is a view in cross section of the liquid flow detector.
Figure 4:
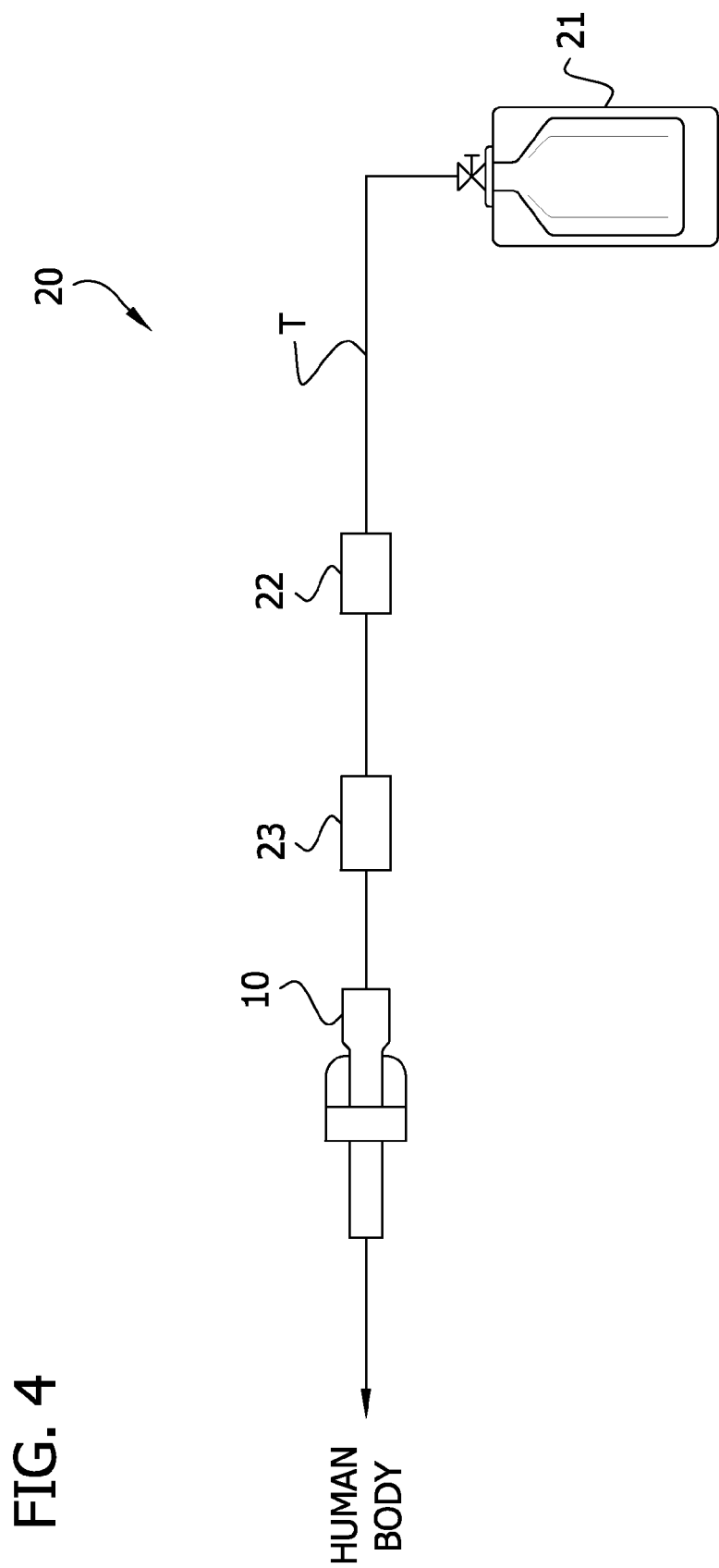
FIG. 4 is a block diagram showing a schematic of the transfusion line set.

A liquid flow detector according to a mode of embodiment of the present invention and a transfusion line provided with the same will be described below in detail with reference to the figures. FIGS. 1 and 2 show a liquid flow detector 10 according to this mode of embodiment, and this liquid flow detector 10 is used in order to detect the flow of a minute amount of a liquid such as a drug solution (referred to hereinbelow as "liquid") which is flowing inside tubes T (which configure the liquid supply channel according to the present invention and are shown in FIG. 4) of a transfusion line set 20. That is to say, the liquid flow detector 10 comprises a detector main body 11; a mobile spherical body 12 arranged inside the detector main body 11 and acting as the mobile body according to the present invention; an inflow pipe 13 provided at the upstream side of the detector main body 11 (the right-hand side in FIGS. 1 and 2; hereinafter, the upstream side of the liquid flow shall be referred to as the rear part, and the downstream side of the liquid flow shall be referred to as the front part); an outflow pipe 14 provided at the downstream side of the detector main body 11; and grip parts 15, 16a, 16b formed on the periphery of the detector main body 11.

The detector main body 11 is cylindrical, and as shown in FIG. 2, it has formed inside it a liquid flow channel 17 comprising a liquid flow detection channel 17a, a discharge channel 17b, and an intermediate flow channel 17c positioned between the liquid flow detection channel 17a and the discharge channel 17b. Furthermore, an upstream hole 18 which links the liquid flow detection channel 17a in communication with an upstream liquid flow channel 13a formed inside the inflow pipe 13 is formed at the upstream end of the liquid flow detection channel 17a, and a downstream hole 19 which links the discharge channel 17b in communication with a downstream liquid flow channel 14a formed inside the outflow pipe 14 is formed at the downstream end of the discharge channel 17b.

The liquid flow detection channel 17a consists of a hole extending from front to rear with a constant diameter (1.6 mm), and it is approximately ⅓ of the length of the liquid flow channel 17 in the front to rear direction (3.0-4.0 mm). The discharge channel 17b consists of a hole extending from front to rear with a constant diameter (2.0 mm), and it is approximately ⅔ of the length of the liquid flow channel 17 in the front to rear direction (7.0-8.0 mm). The intermediate flow channel 17c consists of a hole having a tapering inner peripheral surface, in which the diameter at its upstream end is the same as the diameter of the liquid flow detection channel 17a, and the diameter at its downstream end is the same as the diameter of the discharge channel 17b, and the length of the liquid flow channel 17 in the front to rear direction is set at approximately 10-12 mm.

The upstream hole 18 consists of a hole in which the outer periphery of the face (space) orthogonal to the flow of liquid is elliptical, and the length along the major axis of the ellipse (horizontal direction) is set at 1.2 mm, with the length along the minor axis of the ellipse (vertical direction) being set at 0.8 mm. Furthermore, a step 18a is formed between the liquid flow detection channel 17a and the upstream hole 18. The downstream hole 19 consists of a hole which is larger than the upstream hole 18 in which the outer periphery of the face (space) orthogonal to the flow of liquid is elliptical, and the length along the major axis of the ellipse (horizontal direction) is set at 1.8 mm, with the length along the minor axis of the ellipse (vertical direction) being set at 1.2 mm.

Furthermore, a linking hole 19a which is tapered so as to become steadily narrower from the side of the discharge channel 17b moving towards the side of the downstream hole 19 is formed between the discharge channel 17b and the downstream hole 19. This linking hole 19a has an upstream end formed as a circle having the same diameter as the diameter of the discharge channel 17b, becoming steadily narrower as it approaches the downstream hole 19, and also it becomes an ellipse whereof the major axis in the horizontal direction is longer than the minor axis in the vertical direction. This detector main body 11, and the inflow pipe 13, outflow pipe 14 and grip parts 15, 16a, 16b which will be described later, are made of polycarbonate, polypropylene, or similar polymeric material.

The mobile spherical body 12 is then arranged in the liquid flow channel 17 which is formed in this manner. The mobile spherical body 12 is made of polytetrafluoroethylene, which has excellent resistance to drugs, and the diameter is 1.5 mm, and the specific gravity is 2.13-2.22. It is also possible to use polyacetal (specific gravity 1.41-1.42) or polypropylene (specific gravity 0.90-0.91). Consequently, if the direction of flow of the liquid inside the liquid flow channel 17 is made horizontal, and the mobile spherical body 12 is positioned at the upstream side inside the liquid flow detection channel 17a, there is only a small gap between the inner peripheral surface of the liquid flow detection channel 17a and the outer peripheral surface of the mobile spherical body 12, and therefore the mobile spherical body 12 presents resistance to the flow of liquid and moves to the side of the discharge channel 17b with the flow of liquid, even if the liquid flow rate is minute.

Figure 3:
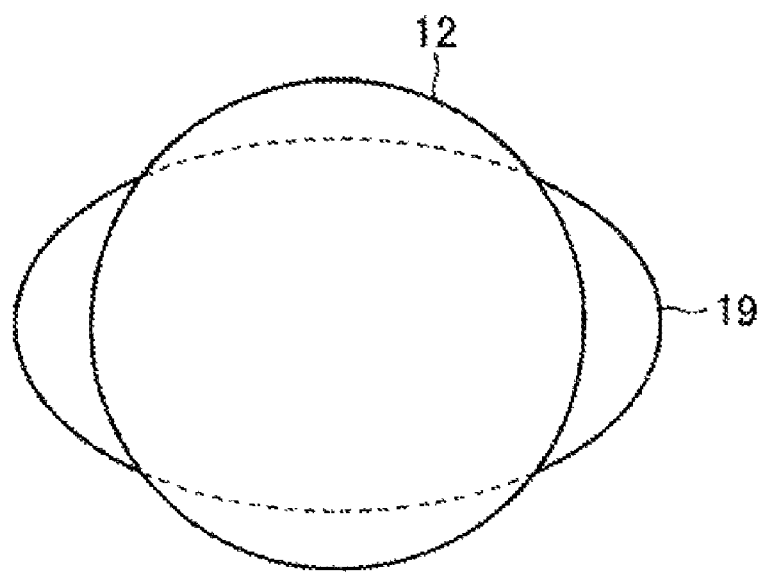
FIG. 3 illustrates the relationship between the downstream hole and the mobile spherical body.

When the mobile spherical body 12 is positioned inside the discharge channel 17b, there is a reasonable size of gap between the inner peripheral surface of the discharge channel 17b and the outer peripheral surface of the mobile spherical body 12, and therefore there is little or no resistance to the flow of liquid due to the mobile spherical body 12. Consequently, the mobile spherical body 12 remains static at the lower part of the inner peripheral surface of the discharge channel 17b, or moves steadily towards the downstream hole 19, depending on the flow rate of the liquid. In this case, the positional relationship between the mobile spherical body 12 and the downstream hole 19 is as shown in FIG. 3, even if the flow rate of liquid is high and the mobile spherical body 12 has reached the opening of the downstream hole 19.

Consequently, the mobile spherical body 12 cannot pass through the downstream hole 19 and move into the downstream liquid flow channel 14a, and only liquid passes through the downstream hole 19 and flows into the downstream liquid flow channel 14a. Furthermore, in the same way, when the liquid flow detection channel 17a is positioned lower down than the discharge channel 17b so that the mobile spherical body 12 reaches the opening of the upstream hole 18, the positional relationship between the mobile spherical body 12 and the upstream hole 18 is as shown in FIG. 3. Consequently, the mobile spherical body 12 cannot pass through the upstream hole 18 and move into the upstream liquid flow channel 13a, and liquid passes through the upstream hole 18 and flows into the liquid flow detection channel 17a.

The inflow pipe 13 consists of a female luer in which the diameter of the upstream liquid flow channel 13a formed therein becomes steadily smaller from the opening side moving towards the side of the upstream hole 18, and a thread 13b (omitted from FIG. 2) is formed on the outer periphery of the opening part. A male luer part which is attached to the tip end of a specific tube T from the plurality of tubes T can be engaged at the inflow pipe 13. Furthermore, the outflow pipe 14 consists of a male bier in which the diameter of the outer peripheral surface of the front end portion (a portion of approximately ⅓ of the whole length) becomes steadily smaller from the base end side towards the front end side of the outflow pipe 14, and a female luer part attached to the tip end of a specific tube T can be engaged at the outflow pipe 14.

The grip part 15 is provided on the outer periphery of a portion of the detector main body 11 on the outflow pipe 14 side, and it is formed as a disc shape. The downstream hole 19, linking hole 19a, downstream end of the discharge channel 17b and upstream end of the downstream liquid flow channel 14a in the detector main body 11 are positioned inside this grip part 15, and the thickness of the grip part 15 corresponds to these. Furthermore, the grip parts 16a, 16b are both formed as plate shapes which project outwards from the outer peripheral surface of the detector main body 11. These grip parts 16a, 16b extend in the axial direction of the detector main body 11 with an interval between each other of 180°, and the front end thereof reaches the rear surface of the grip part 15. The grip part 15 or grip parts 16a, 16b are gripped with the hand when the liquid flow detector 10 is operated.

The liquid flow detector 10 configured in this way is incorporated into the transfusion line set 20 shown in FIG. 4. This transfusion line set 20 configures the transfusion line according to the present invention and comprises an infuser 21, a filter 22 and a flow restriction filter 23, and the liquid flow detector 10 is arranged downstream of the flow restriction filter 23. Each device of the transfusion line set 20 is then connected by means of specific tubes T. The infuser 21 is provided with an expandable liquid container and an open/close operating part for opening and closing the liquid container, and liquid is housed inside the liquid container. Then, when the outflow port of the liquid container is opened by operation of the open/close operating part, the liquid is pushed out by the force of contraction of the liquid container.

The filter 22 absorbs foreign bodies in the liquid delivered from the infuser 21, removing them from the liquid. The flow rate restriction filter 23 makes the flow rate of the liquid delivered from the infuser 21, via the filter 22, constant, and it sends it to the liquid flow detector 10 on the downstream side. The liquid flow detector 10 allows the liquid to pass through, and is operated when the flow of liquid is to be confirmed, as required. The liquid which has passed through the liquid flow detector 10 is then supplied to the patient's body. That is to say, when the transfusion line set 20 is used, the downstream end of the tube T is connected to a puncture needle (not depicted) such as an indwelling needle which pierces the patient's body and remains indwelling.

Next, drug solution flows from the infuser 21 into each of the tubes T, and the air inside each of the devices which make up the transfusion line set 20 is flushed out, after which the flow of liquid is stopped for a time. In this state, a puncture needle is made to pierce a specific point on the patient's body, and liquid once again flows into the tubes T etc. By means of this, liquid at a set and constant flow rate is supplied to the patient's body from the infuser 21. At this time, the liquid flow detection channel 17a is preferably positioned higher up than the discharge channel 17b, and the mobile spherical body 12 is preferably positioned inside the discharge channel 17b. By means of this, it is possible to reliably prevent the mobile spherical body 12 from obstructing the flow of liquid inside the liquid flow detector 10. Then, if necessary, it can be confirmed whether or not the liquid is flowing properly using the liquid flow detector 10.

In this case, the mobile spherical body 12 is first of all moved to the upstream end of the liquid flow detection channel 17a by inclining the liquid flow detector 10 so that the liquid flow detection channel 17a is lower than the discharge channel 17b. Once the mobile spherical body 12 has reached the upstream end of the liquid flow detection channel 17a, the liquid flow detector 10 is placed on a base or the like having a horizontal surface, and the direction of flow of the liquid inside the liquid flow channel 17 is set to the horizontal. In this case, when the mobile spherical body 12 is moved inside the liquid flow detection channel 17a towards the discharge channel 17b, it is judged that the liquid is flowing properly. Furthermore, if the mobile spherical body 12 is static, it is judged that the liquid is not flowing, and the necessary steps are taken. If it is judged that the liquid is flowing properly, the liquid flow detection channel 17a is preferably once again positioned higher up than the discharge channel 17b, and the mobile spherical body 12 is preferably positioned inside the discharge flow channel 17b.

As described above, with the liquid flow detector 10 according to this mode of embodiment, the liquid flow channel 17 comprising the liquid flow detection channel 17a, discharge channel 17b and intermediate flow channel 17c, is formed inside the detector main body 11, and the mobile spherical body 12 is arranged inside said flow channel 17. Then, the diameter of the liquid flow detection channel 17a is set to be slightly greater than the diameter of the mobile spherical body 12, and the diameter of the discharge channel 17b is set to be even greater than the diameter of the liquid flow detection channel 17a. Accordingly, when the mobile spherical body 12 is positioned at the upstream end of the liquid flow detection channel 17a in a state in which the liquid flow channel 17 of the detector main body 11 is horizontally positioned, the mobile spherical body 12 moves from the upstream side towards the downstream side of the liquid flow detection channel 17a when the liquid is flowing properly inside the liquid flow channel 17 from the upstream side towards the downstream side.

By means of this it is possible to detect that the liquid is flowing inside the liquid flow channel 17. Furthermore, when the mobile spherical body 12 is positioned inside the discharge channel 17b, there is a large gap between the inner peripheral surface of the discharge channel 17b and the outer peripheral surface of the mobile spherical body 12, and therefore there is no obstruction to the flow of liquid. Furthermore, the peripheral edge parts of the upstream hole 18 and downstream hole 19 which are provided at both ends of the liquid flow channel 17 are formed as an ellipse, and therefore it is possible to prevent the mobile spherical body 12 from moving outside of the liquid flow channel 17, and also to prevent the flow of liquid stopping because of the mobile spherical body 12 coming into abutment with the peripheral edge parts of the upstream hole 18 or downstream hole 19. Furthermore, the tapering intermediate flow channel 17c is provided between the liquid flow detection channel 17a and the discharge channel 17b, and therefore it is possible to carry out a smooth operation to move the mobile spherical body 12 from the discharge channel 17b to the liquid flow detection channel 17a.

Furthermore, the liquid flow detector 10 according to the present disclosure is not limited to the mode of embodiment described above, and suitable modifications can be implemented. For example, in the mode of embodiment described above, the diameter of the liquid flow detection channel 17a is set at 1.6 mm, and the diameter of the mobile spherical body 12 is set at 1.5 mm, but both of these diameters may be suitably modified depending on the flow rate of the liquid. If the flow of liquid is no more than 1 ml per hour, for example, the diameter of the liquid flow detection channel 17a and the diameter of the mobile spherical body 12 are set so that the area of the minimum gap between the inner peripheral surface of the liquid flow detection channel 17a and the outer peripheral surface of the mobile spherical body 12 is even smaller.

Furthermore, if the flow of liquid is greater than 1 ml per hour, the diameter of the liquid flow detection channel 17a and the diameter of the mobile spherical body can be set so that the area of the minimum gap between the inner peripheral surface of the liquid flow detection channel 17a and the outer peripheral surface of the mobile spherical body 12 is slightly greater. In addition, in the mode of embodiment described above, the shape of the peripheral edge part of the upstream hole 18 and downstream hole 19 is made elliptical so that liquid passes through without being obstructed by the mobile spherical body 12, but the mobile spherical body 12 does not pass through; other shapes may, however, be employed instead of this.

For example, it is possible to allow only liquid to pass through by providing a groove part at the peripheral edge part of circular holes, or similar. Furthermore, it is possible to allow only liquid to pass through by providing the circular holes with a filter. In addition, in the mode of embodiment described above, the mobile body is configured by the mobile spherical body 12, but a columnar body, a body in which the centre axis of two conical bodies has been placed coaxially and the tops of the two conical bodies are linked, or a body in which the centres of two facing discs are linked by a shaft, or similar can also be used instead of the mobile spherical body 12. Furthermore, the mobile body may be moved by forming the face on the upstream side of the mobile body as a recess instead of a convex surface or plane surface, and making the liquid come into contact with the recess. In addition, the diameter of the discharge flow channel 17b may be set so that the downstream side is larger than the upstream side, and the inner peripheral surface of the discharge channel 17*b* may be tapered. In this case, the intermediate flow channel 17*c* may be omitted. In addition, the structure and material of the various members making up the liquid flow detector 10, and the specific gravity etc. of the mobile spherical body 12 may be suitably modified within the technical scope of the present disclosure.

What is claimed is:

1. A fluid flow detector for detecting the flow of a fluid in a transfusion line, comprising:
    a detector main body defining a fluid flow channel having a circular cross section and comprising, an upstream hole formed at an upstream end of the detector main body, a downstream hole formed at a downstream end of the detector main body, a fluid flow detection channel positioned adjacent the upstream hole, a discharge channel positioned adjacent the downstream hole, and an intermediate flow channel provided between the fluid flow detection channel and the discharge channel; and
    a mobile body positioned within the fluid flow channel and dimensioned to be movable along the fluid flow channel in response to the flow of a fluid inside the fluid flow channel, and in which an outer peripheral edge part of a face of the fluid flow channel which is orthogonal to the direction of movement is formed to be circular;
    wherein the diameter of the fluid flow detection channel is smaller than the diameter of the discharge channel, and the maximum diameter of the outer peripheral edge part of the face of the fluid flow channel orthogonal to the direction of movement of the mobile body is set to be slightly smaller than the diameter of the fluid flow detection channel, and the upstream hole and the downstream hole are formed with a size and shape such that fluid can flow around the mobile body through the upstream and downstream holes;
    wherein the intermediate flow channel has a diameter that becomes steadily greater from the fluid flow detection channel towards the discharge channel;
    wherein the intermediate flow channel has a length in a longitudinal direction that is smaller than the diameter of the outer peripheral edge part of the mobile body; and
    wherein the fluid flow detection channel, the discharge channel, and the intermediate flow channel, are arranged in a straight line.

2. A fluid flow detector according to claim 1, in which the mobile body consists of a spherical body.

3. A fluid flow detector according to claim 1, wherein the fluid flow channel from between the upstream hole and the downstream hole consists of a shape in which the peripheral edge part of the upstream hole and downstream hole orthogonal to the flow of fluid is elliptical.

4. A fluid flow detector according to claim 1, in which an inflow pipe comprising a female luer which links in communication with the fluid flow channel is joined to the upstream hole of the detector main body, and an outflow pipe comprising a male luer which links in communication with the fluid flow channel is joined to the downstream hole of the detector main body.

5. A fluid flow detector according to claim 1, wherein the fluid flow detector is incorporated into a transfusion line that includes a fluid supply part and a fluid supply channel through which passes a fluid supplied from the fluid supply part, and the fluid flow detector is arranged in the fluid supply channel.

6. A fluid flow detector, comprising:
    a detector main body defining a fluid flow channel having an upstream end and an downstream end, the fluid flow channel defining a fluid flow detection channel disposed on the upstream end, a discharge channel disposed on the downstream end, and an intermediate flow channel provided between the fluid flow detection channel and the discharge channel; and
    a mobile body movably disposed within the fluid flow channel between the fluid flow detection and discharge channels, wherein the discharge channel has a diameter larger than the fluid flow detection channel, and wherein the mobile body is configured to be selectively positioned within the fluid flow detection channel to provide indicia of fluid flow within the fluid flow detection channel;
    wherein the intermediate flow channel has a diameter that becomes steadily greater from the fluid flow detection channel towards the discharge channel;
    wherein the intermediate flow channel has a length in a longitudinal direction that is smaller than the diameter of the outer peripheral edge part of the mobile body; and
    wherein the fluid flow detection channel, the discharge channel, and the intermediate flow channel, are arranged in a straight line.

7. A fluid flow detector according to claim 6, wherein the mobile body is positioned to move towards the discharge channel in response to gravitational force acting on the mobile body when the detector main body is disposed in an initial position.

8. A fluid flow detector according to claim 6, wherein the diameter of the fluid flow detection channel is slightly larger than the diameter of the mobile body so that fluid may flow past the mobile body within the fluid flow detection channel.

9. A fluid flow detector according to claim 6, wherein the mobile body is shaped and dimensioned to enable fluid to flow through the fluid flow channel at a predetermined minimum flow rate.

10. A fluid flow detector according to claim 6, wherein the mobile body is spherically shaped.

11. A fluid flow detector according to claim 6, wherein the fluid flow channel is dimensioned to accommodate a predetermined minimum flow rate of between about 0.1 ml/hr and about 20 ml/hr.

12. A fluid flow detector according to claim 6, wherein at least one of the fluid flow detection and discharge channels of the fluid flow channel is configured to be visually perceptible to a user.

13. A fluid flow detector according to claim 6, wherein the fluid flow channel is configured to receive a drug solution for passage to a patient's body.

14. A fluid flow detector according to claim 6, wherein at least one of the upstream end and the downstream end of the fluid flow channel is configured to engage a medical device.

* * * * *